(12) United States Patent
Lee et al.

(10) Patent No.: US 11,794,002 B2
(45) Date of Patent: Oct. 24, 2023

(54) NEUROMODULATION PROBE

(71) Applicant: Industrial Technology Research Institute, Hsinchu (TW)

(72) Inventors: Jo-Ping Lee, Hsinchu (TW); Chieh-Feng Chang, Changhua County (TW); Chung-Hsin Su, Hsinchu (TW); Kun-Ta Wu, Nantou County (TW); Chii-Wann Lin, Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 17/546,725

(22) Filed: Dec. 9, 2021

(65) Prior Publication Data

US 2022/0184382 A1 Jun. 16, 2022

Related U.S. Application Data

(60) Provisional application No. 63/125,424, filed on Dec. 15, 2020.

(30) Foreign Application Priority Data

Aug. 23, 2021 (TW) .................................. 110131073

(51) Int. Cl.
*A61N 1/05* (2006.01)
(52) U.S. Cl.
CPC .................................. *A61N 1/0534* (2013.01)

(58) Field of Classification Search
CPC .............. A61N 1/0534; A61N 1/36067; A61N 1/36182; A61N 1/40; A61N 2/006; A61N 2/02
See application file for complete search history.

(56) References Cited

U.S. PATENT DOCUMENTS

| 4,412,540 A | 11/1983 | Bentall |
| 7,869,882 B2 | 1/2011 | DeRidder |
| 8,000,794 B2 | 8/2011 | Lozano |
| 9,610,459 B2 | 4/2017 | Burnett et al. |
| 10,213,615 B2 | 2/2019 | Gale et al. |

(Continued)

FOREIGN PATENT DOCUMENTS

| CN | 101888875 A | 11/2010 |
| CN | 103143114 A | 6/2013 |

(Continued)

OTHER PUBLICATIONS

TW OA issued on Apr. 13, 2022.
(Continued)

*Primary Examiner* — Ankit D Tejani
*Assistant Examiner* — Joshua Brendon Solomon
(74) *Attorney, Agent, or Firm* — WPAT, P.C

(57) ABSTRACT

A neuromodulation probe includes a body and at least one coil set. The body has a first axis and a length along the first axis. The at least one coil set includes at least one coil, and the at least one coil is formed by winding spirally a conductive wire plural times about a second axis inside the body or on an outer surface of the body. The second axis is parallel to the first axis. The at least one coil has two opposite wire ends for providing an electric current to flow in or out of the at least one coil.

11 Claims, 11 Drawing Sheets

(56) References Cited

U.S. PATENT DOCUMENTS

| | | | |
|---|---|---|---|
| 10,307,604 B2 | 6/2019 | Hastings et al. | |
| 10,350,420 B2 | 7/2019 | Carbunaru et al. | |
| 10,589,085 B2 | 3/2020 | Young et al. | |
| 10,603,498 B2 | 3/2020 | Blum et al. | |
| 2005/0177209 A1* | 8/2005 | Leung | A61B 18/148 607/101 |
| 2007/0203540 A1 | 8/2007 | Goetz et al. | |
| 2011/0301665 A1* | 12/2011 | Mercanzini | A61B 5/6868 607/45 |
| 2018/0353766 A1* | 12/2018 | Casse | A61N 2/02 |

FOREIGN PATENT DOCUMENTS

| | | |
|---|---|---|
| CN | 102847231 B | 2/2015 |
| CN | 105194796 A | 12/2015 |
| CN | 107080561 A | 8/2017 |
| CN | 110433396 A | 11/2019 |
| CN | 108712921 B | 5/2020 |
| CN | 112601488 A | 4/2021 |
| TW | I442905 | 7/2014 |
| TW | I528984 | 4/2016 |
| TW | I541045 B | 7/2016 |

OTHER PUBLICATIONS

Lee et al. "Implantable microcoils for intracorticalmagnetic stimulation", Dec. 9, 2016, pp. 1-14, Science Advances Research Article.

\* cited by examiner

NEUROMODULATION PROBE

CROSS REFERENCE TO RELATED APPLICATION

This application claims the benefits of U.S. provisional application No. 63/125,424, filed on Dec. 15, 2020, and Taiwan application Ser. No. 110131073, filed on Aug. 23, 2021, the disclosures of which are incorporated by references herein in its entirety.

TECHNICAL FIELD

The present disclosure relates in general to a device of medical technology, and more particularly to a neuromodulation probe.

BACKGROUND

In the art, nuclei in the brain are connected to each other via nerve fibers. By having the subthalamic neucleus (STN) as an example, in order to promote smoothness of movement, the subthalamic neucleus would generate electric signals to activate corresponding nuclei, such as the internal globus pallidus (GPi). Through activating the GPi, the putamen would produce dopamine secretion, and the dopamine would affect initiation and termination of the movement. If the neural network for transmitting the dopamine cannot be well activated, then insufficient dopamine secretion would lead to some clinical symptoms such as stiffness or trembling, which are deemed as typical symptoms of Parkinson's disease.

Beside relevant medications, the implantable neural electrical stimulation is introduced to stimulate the subthalamic neucleus or the internal globus pallidus for further activating the corresponding neural networks, such that movement disorders can be improved. In a preliminary test for side effects induced by electrical stimulation after implanting the electrodes, the limb muscle tension and the brainwave response to light are investigated.

Since the subthalamic neucleus and the internal globus pallidus are communicated through particular nerve fibers, and clinically it is found in some examples that better electrical stimulation performance can be achieved while the implanted electrodes exert stimulation at an upper external side of the subthalamic neucleus. However, in the upper external side of the subthalamic neucleus, there exists internal capsules of the nerve fibers. If these nerve fibers are stimulated to induce a potential to activate a downward motion, then unexpected side effects such as muscle stiffness may arise. Thus, the nerve stimulation shall be performed accurately so as to reduce possible side effects, and also to elevate neuromodulation.

In addition, the modulation process of electrical stimulation shall controlled the stimulation right within a therapeutic window. If the neuromodulation is not well controlled, then side effects would be induced. In other words, to avoid side effects producing, the degree of electrical stimulation shall be limited.

Further, if the electric current coil is extended in parallel to the nerve fiber to be stimulated, then change in the action potential would be induced at this nerve fiber.

Currently, the directional electrode is applied to reduce the side effects. However, since the optimal stimulation point is close to the internal capsule, the magnetic field of the directional electrode would affect the internal capsule and the associated nerve fiber. Namely, in the case that the directional electrode is applied to accurately perform the electrical stimulation and also to avoid side effects, a risk of stimulating that a non-target region cannot be waived.

Accordingly, how to develop a device that can polarize the nerve fiber in a specific anatomical direction to generate an action potential, and form an electrical stimulation with a selective direction to achieve precise stimulation, reduce side effects, and improve the effect of neuromodulation, is an issue needed to be solved urgently for the skilled person in the art.

SUMMARY

In one embodiment of this disclosure, a neuromodulation probe includes:
  a body, having a first axis and a length along the first axis; and
  at least one coil set, including at least one coil, the at least one coil being formed by winding spirally a conductive wire plural times about a second axis inside the body or on an outer surface of the body, the second axis being parallel to the first axis, wherein the at least one coil has two opposite wire ends for providing an electric current to flow in or out of the at least one coil.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DETAILED DESCRIPTION

Figure 1A:
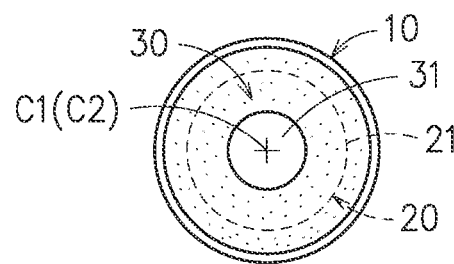
FIG. 1A is a schematic top view of FIG. 1.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 1:
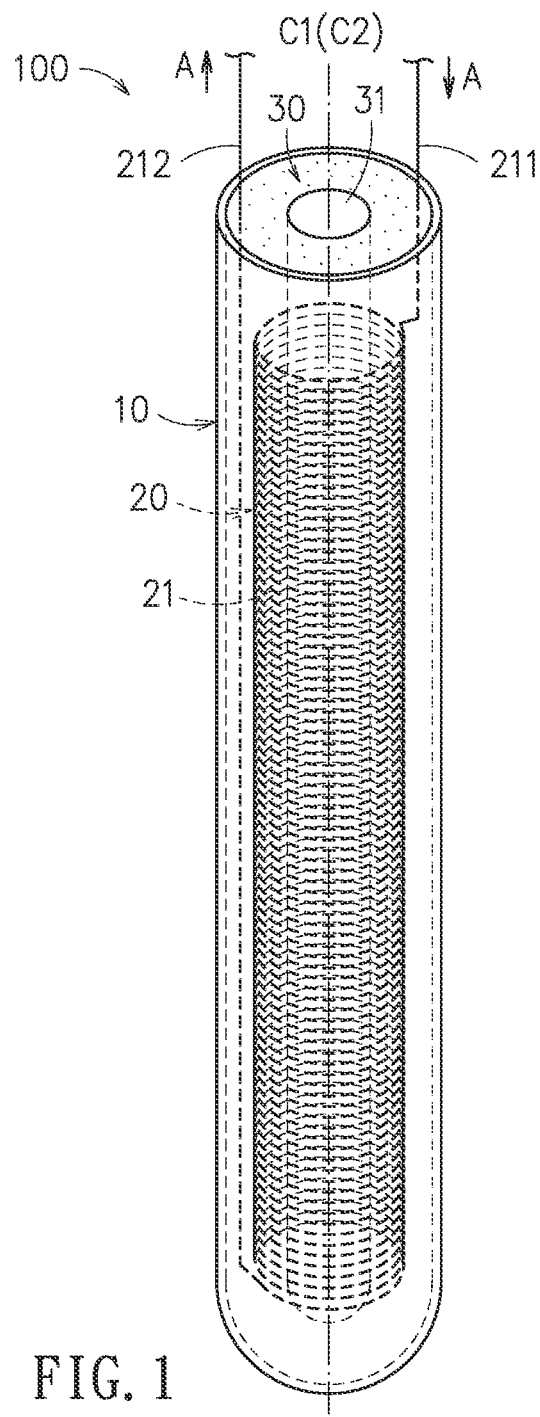
FIG. 1 is a schematic perspective of an embodiment of the neuromodulation probe in accordance with this disclosure.
Figure 1B:
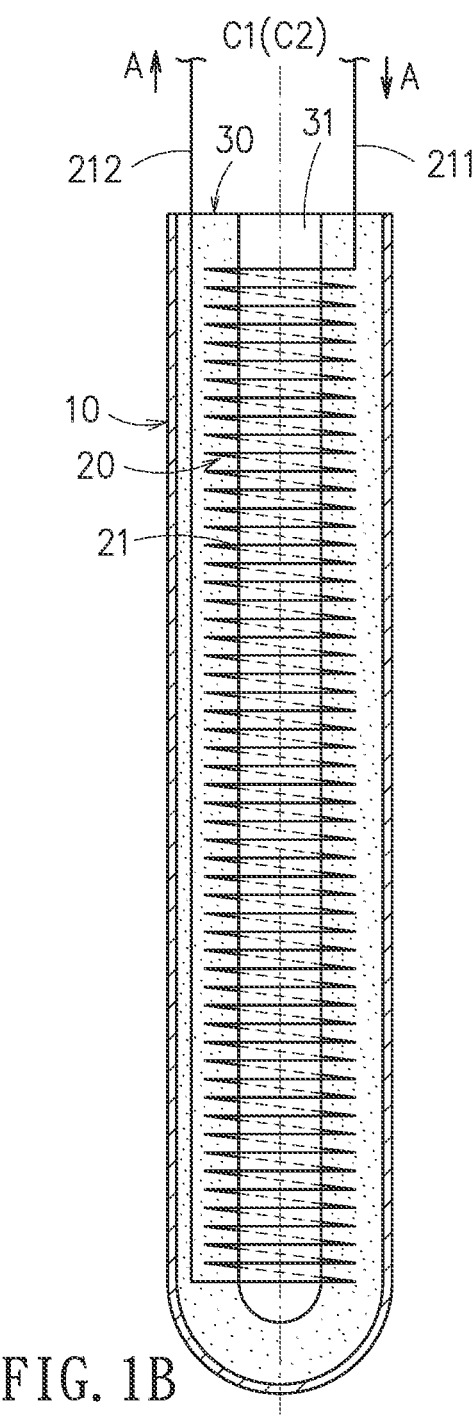
FIG. 1B is a schematic cross-sectional view of FIG. 1 along the first axis.

Referring to FIG. 1, FIG. 1A and FIG. 1B, a neuromodulation probe 100 of this embodiment includes a body 10 and a coil set 20. This neuromodulation probe 100 can be applied to connect a power source (not shown in the figure), and the power source provides an electric current to the neuromodulation probe 100 so as to stimulate electrically nerve fibers surrounding the neuromodulation probe 100.

The body 10, made of a bio-compatible material, is defined along a first axis C1 to extend therealong a length.

The coil set 20 includes a coil 21 coated with an insulation layer or a polymer layer. The coil 21 is formed by having a conductive wire to wind plural times around a second axis C2 inside the body 10. The second axis C2 is parallel to the first axis C1. In this embodiment, both cross sections the body 10 and the coil 21 are regularly circular, and the second axis C2 and the first axis C1 are coaxial. Namely, the coil 21 can be interpreted to wind spirally along the first axis C1. The winding direction of the coil 21 is roughly perpendicular to the first axis C1 (equivalent to the second axis C2), and the extension direction thereof is parallel to the first axis C1 (i.e., the second axis C2).

The coil 21 of the coil set 20 is fixed inside the body 10 by a fixing glue 30, such that the coil set 20 can be prevented from being loosened or dropped off from the body 10. According to this disclosure, the body 10 is furnished thereinside with an internal lengthy space 31 extending along the first axis C1. In this embodiment, the internal lengthy space 31 penetrates through the coil 21 (i.e., along the second axis C2). In another embodiment, the internal lengthy space 31 can provide a channel (not labeled in the figure) for introducing a coolant into the body 10 to avoid overheating while the neuromodulation probe 100 is operated.

Two opposite wire ends 211, 212 of the coil 21 are applied to provide an electric current A to flow in or out from the coil 21. As shown in FIG. 1, the electric current A flows into the coil 21 via the wire end 211 at a leading end of the coil 21, and leaves the coil 21 via the wire end 212 at a tailing end thereof. In addition, the electric current A can flow in a reverse direction. Namely, the electric current A can flow into the coil 21 from the tailing wire end 212, and leaves the coil 21 via the leading wire end 211.

Since the winding direction of the coil 21 is roughly perpendicular to the first axis C1, thus the flow direction of the electric current A in the coil 20 would be also roughly perpendicular to the first axis C1.

The intensity, frequency, flow direction of the electric current A, the wire diameter, pitch diameter and winding number of the coil 21, and the length and diameter of the body 10 are not specifically limited, but determined per practical requirements for achieving necessary stimulation intensity, according to this disclosure.

Figure 2:
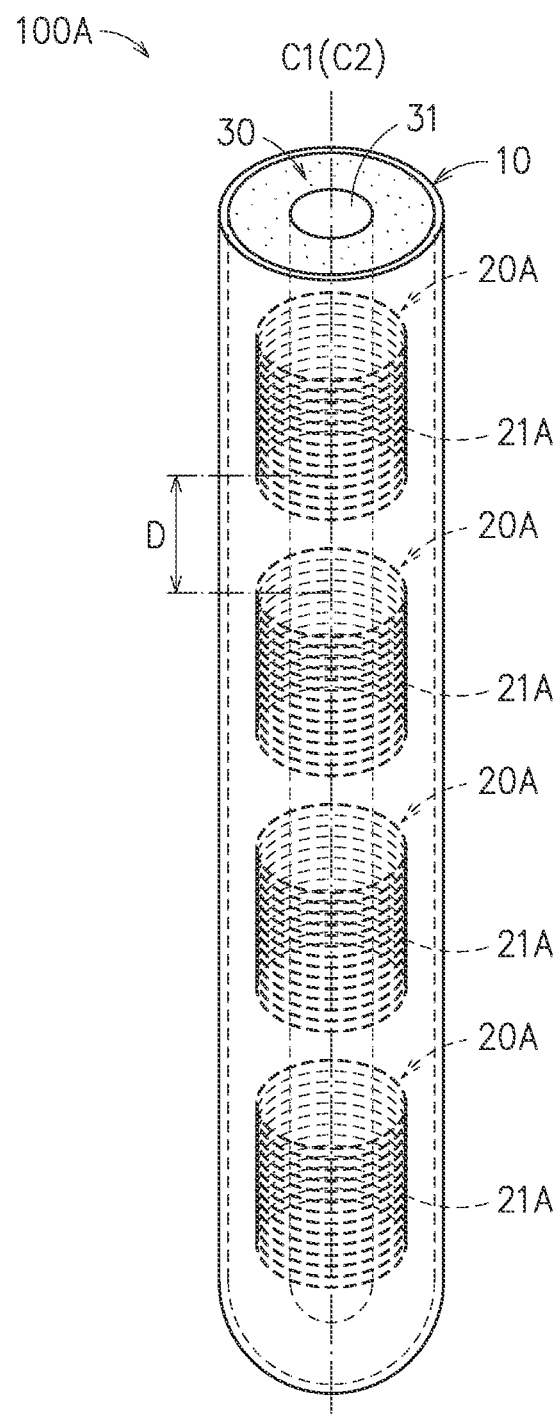
FIG. 2 is a schematic perspective of another embodiment of the neuromodulation probe in accordance with this disclosure.

Referring to FIG. 2, in this embodiment, the neuromodulation probe 100A includes a body 10 and a plurality of coil sets 20A coaxially and orderly disposed along a first axis C1. The difference between the embodiment of FIG. 2 and that of FIG. 1 is at the length and number of the coils.

As shown in FIG. 2, each of the coil sets 20A has a plurality of coils 21A, and each of the coils 21A has two opposite ends applied for allowing the electric current to flow in and out of the coil 21A, respectively. Since this embodiment is roughly resembled to that of FIG. 1, and thus details about the embodiment of FIG. 2 would be omitted herein.

Central axes of the coils 21A are colinear to form a second axis C2, coaxial with the first axis C1 of the body 10. Every two neighboring coils 21A are spaced by a respective distance D, and all the distances D might be the same or different to each other. In this embodiment, the distance D is greater than zero. If all the distances D of FIG. 2 are equal to zero, then this embodiment is just that of FIG. 1.

In the embodiment of FIG. 2, the electric current of each the coil 21A of the coil sets 20A can be separately controlled, and the intensities, frequencies and flow directions of the electric currents of the individual coils 21A can be the same or different to each other.

The coil sets 20A are fixed inside the body 10 by a fixing glue 30. In this embodiment, the body 10 is furnished thereinside with an internal lengthy space 31 extending along the first axis C1 for containing a coolant in the body 10.

Figures 3, 3A:
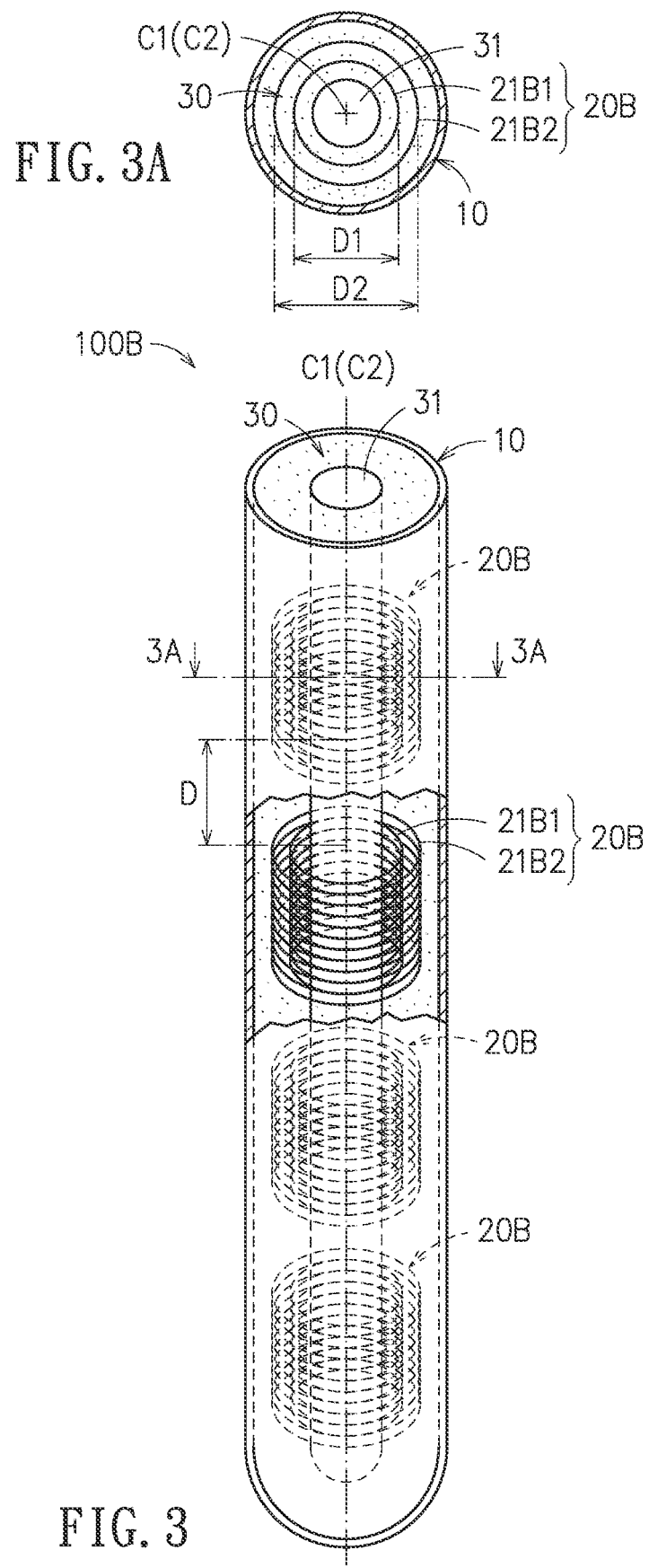
FIG. 3 is a schematic perspective of a further embodiment of the neuromodulation probe in accordance with this disclosure, with a portion thereof in a cross-sectional view.
FIG. 3A is a schematic cross-sectional view of FIG. 3 along line 3A-3A.

Referring to FIG. 3 and FIG. 3A, in this embodiment, the neuromodulation probe 100B includes a body 10 and a plurality of coil sets 20B coaxially and orderly disposed along a first axis C1.

Each of the coil sets 20B has two coils 21B1, 21B2 coaxially sleeved to each other along and centered at the second axis C2 (I.e., the first axis C1). Each of the coils 21B1, 21B2 has two opposite wire ends for providing current to flow in or out of the coil 21B1 or 21B2. Since this embodiment is roughly resembled to that of FIG. 1, and thus details about the embodiment of FIG. 3 and FIG. 3A would be omitted herein.

The second axis C2 of the coils 21B1, 21B2 is coaxial with the first axis C1 of the body 10, the neighboring coil sets 20B are spaced by respective distances D, and these distances D can be the same or different.

In the embodiment of FIG. 3 and FIG. 3A, the electric current of each the coil 21B1 or 21B2 of each the coil set 20B can be separately controlled, and the intensities, frequencies and flow directions of the electric currents of the individual coils 21B1, 21B2 can be the same or different to each other.

The coil sets 20B are fixed inside the body 10 by a fixing glue 30. In this embodiment, the body 10 is furnished thereinside with an internal lengthy space 31 extending along the first axis C1 for containing a coolant in the body 10.

Figures 4, 4A:
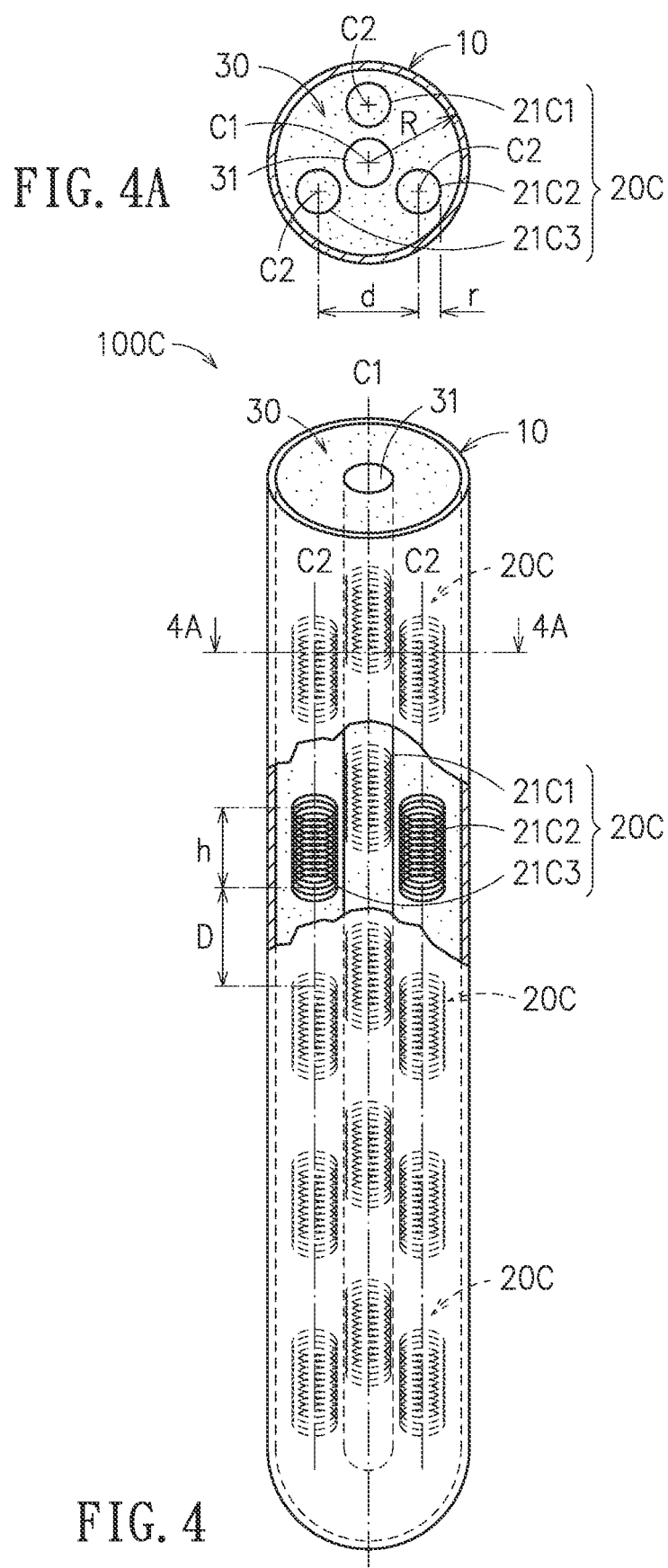
FIG. 4 is a schematic perspective of one more embodiment of the neuromodulation probe in accordance with this disclosure, with a portion thereof in a cross-sectional view.
FIG. 4A is a schematic cross-sectional view of FIG. 4 along line 4A-4A.

Referring to FIG. 4 and FIG. 4A, in this embodiment, the neuromodulation probe 100C includes a body 10 and a plurality of coil sets 20C.

In this embodiment, each of the coil sets 20C has three coils 21C1, 21C2, 21C3, neighbored to each other and arranged to surround the first axis C1 of the body 10. Each of the coil 21C1, 21C2 or 21C3 has two opposite wire ends for providing the electric current to flow in or out of the respective coil. Since this embodiment is roughly resembled to that of FIG. 1, and thus details about the embodiment of FIG. 4 and FIG. 4A would be omitted herein.

The second axes C2 for the respective coils 21C1, 21C2, 21C3 are all parallel to the first axis C1 of the body 10. These three coils 21C1, 21C2, 21C3 of the same coil set 20C are radially arranged evenly. Any two neighboring coils 21C1, 21C2, 21C3 are separated by corresponding distances D, and these distances might be the same or different.

These coils 21C1, 12C2, 21C3 of the same coil set 20C can be arranged to be radially offset or irregularly arranged.

In the embodiment of FIG. 4, the electric current of each the coil 21C1, 21C2 or 21C3 of each the coil set 20C can be separately controlled, and the intensities, frequencies and flow directions of the electric currents of the individual coils 21C1, 21C2, 21C3 can be the same or different to each other.

The coil sets 20C are fixed inside the body 10 by a fixing glue 30. In this embodiment, the body 10 is furnished thereinside with an internal lengthy space 31 extending along the first axis C1 for containing a coolant in the body 10.

Figure 5:
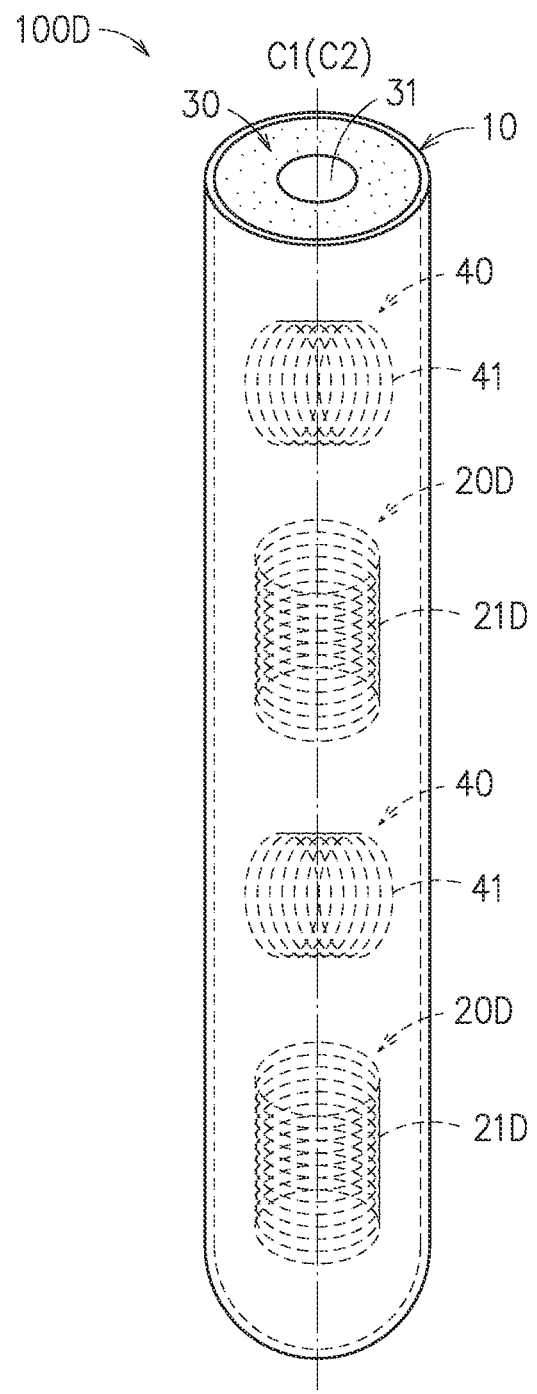
FIG. 5 demonstrates an exemplary example schematically of this disclosure that the body is furnished thereinside with the coil sets and the sub coil sets.

Referring to FIG. 5, in thus embodiment, the neuromodulation probe 100D includes a body 10, two coil sets 20D and two sub coil sets 40. The two sub coil sets 40 and the coil sets 20D are arranged in an interleaved setting manner in the body 10.

The coil set 20D includes a plurality of coils 21D, and each of the coils 21D is formed by circling a conductive wire about a second axis C2 plural times inside the body 10. The connection line of central axes of individual coils 21D (i.e., the second axis C2) is coaxial with the first axis C1 of the body 10. The sub coil set 40 includes a plurality of sub coils 41, and each of the sub coils 41 is formed by winding a conductive wire about a third axis C3 plural times inside the body 10. Each of the coils 21D and the sub coils 41 is coated with an insulation layer a polymer layer.

The third axis C3 is perpendicular to the first axis C1. In other words, the third axis C3 of the sub coil 31 is perpendicular to the second axis C2 of the coil set 20D.

Each of the coils 21D and the sub coils 41 has two opposite wire ends for allowing the electric current to flow in and out of the respective coil 21D or sub coil 41. Since this embodiment is roughly resembled to that of FIG. 1, and thus details about the embodiment of FIG. 5 would be omitted herein.

In the embodiment of FIG. 5, the electric current of each the coil 21D of the coil set 20D or each the sub coil 41 of the sub coil set 40 can be separately controlled, and the intensities, frequencies and flow directions of the electric currents of the individual coils 21D and sub coils 41 can be the same or different to each other.

In this embodiment, the coil sets 20D are fixed inside the body 10 by a fixing glue 30. In addition, the body 10 is furnished thereinside with an internal lengthy space 31 extending along the first axis C1 for containing a coolant in the body 10. In such a circumstance, the sub coil 41 may be disposed by closing to one side of the internal lengthy space 31.

Figure 6:
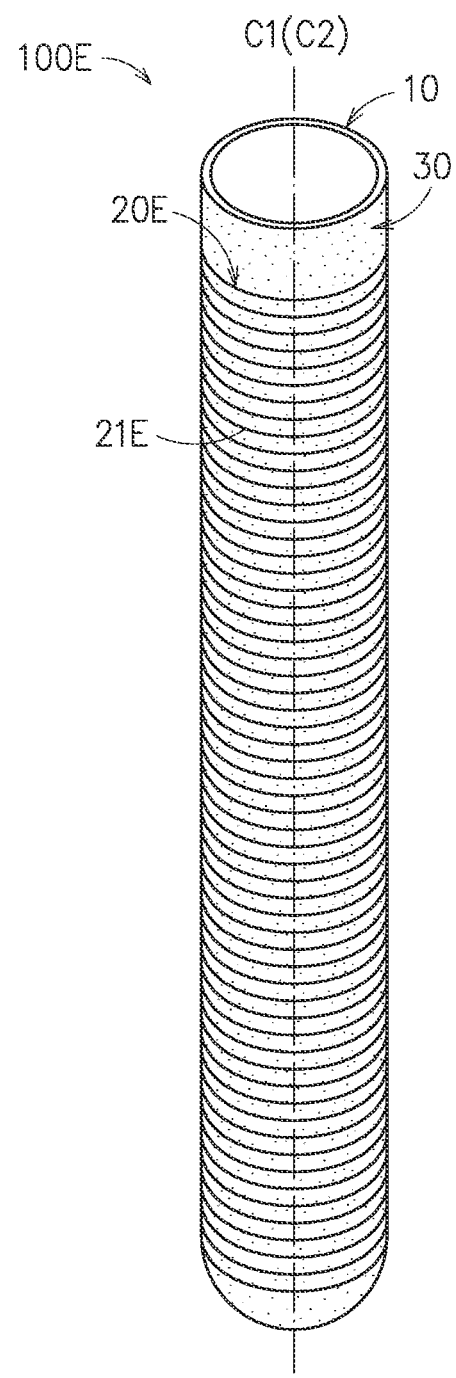
FIG. 6 and FIG. 7 demonstrate schematically two different exemplary examples of this disclosure that the outer surfaces of the respective bodies are wound with different coil sets.

Referring now to the embodiment shown in FIG. 6, the neuromodulation probe 100E includes a body 10 and a coil set 20E. The coil set 20E includes a coil 21E formed by winding a conductive wire on an outer surface of the body 10 plural times about a second axis C2, and a fixing glue 30 is introduced to fix the coil 21E onto the outer surface of the body 10. In this embodiment, the second axis C2 of the coil 21E and the first axis C1 of the body 10 are coaxial.

It shall be noted that, in the embodiment of FIG. 1, the coil set 20 is disposed in the body 10. However, in the embodiment of FIG. 6, the coil set 20E is disposed on the outer surface of the body 10.

The coil 21E has two opposite wire ends applied to provide the electric current to flow in or out of the coil. Since this embodiment is roughly resembled to that of FIG. 1, and thus details about the embodiment of FIG. 6 would be omitted herein.

Figure 7:
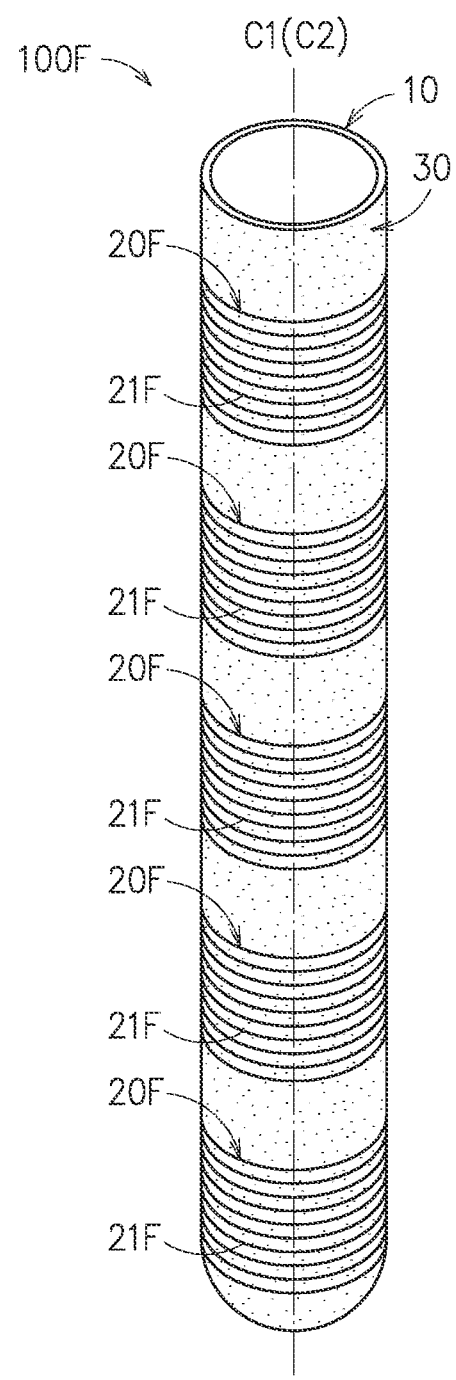

Referring now to the embodiment shown in FIG. 7, the neuromodulation probe 100F includes a body 10 and a plurality of coil sets 20F. Each of the coil sets 20F includes a coil 21F formed by winding a conductive wire plural times on an outer surface of the body and about a second axis C2, and a fixing glue 30 is applied to fix the coil 21F onto the outer surface of the body 10. In addition, the second axis C2 of the coil 21F and the first axis C1 of the body 10 are coaxial.

It shall be noted that, in the embodiment of FIG. 2, the coil set 20A is disposed in the body 10. However, in the embodiment of FIG. 7, the coil set 20F is disposed on the outer surface of the body 10.

The coil 21F has two opposite wire ends applied to provide the electric current to flow in or out of the coil. Since this embodiment is roughly resembled to that of FIG. 1, and thus details about the embodiment of FIG. 7 would be omitted herein.

In the embodiments of FIG. 6 and FIG. 7, structuring of the embodiments of FIG. 3 and FIG. 5 can be applied. For example, one of the coil such as the coil 21B1 of FIG. 3 can be disposed inside the body 10, while another coil such as the coil 21B2 is disposed on the outer surface of the body 10. Also, for another example, the sub coil 41 of FIG. 5 can be disposed inside the body 10, while the coil 21D is disposed on the outer surface of the body 10.

Figure 8A:
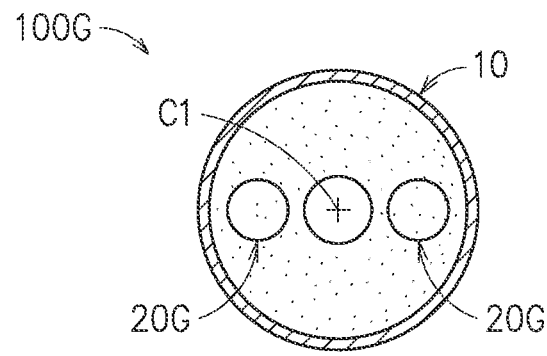
FIG. 8A is a schematic cross-sectional view of an exemplary example of this disclosure that two coil sets are symmetrically provided with respect to the first axis.

Referring now to the embodiment shown in FIG. 8A, the neuromodulation probe 100G includes a body 10 and two coil sets 20G arranged symmetrically to opposite sides of the first axis C1 of the body 10. Each of the two coil sets 20G can include the same coil 21 of FIG. 1, the same coils 21A of FIG. 2, the same coils 21B1, 21B2 of FIG. 3, or the same sub coil sets 40 of FIG. 5 arranged in the same interleaved setting manner.

Figure 8B:
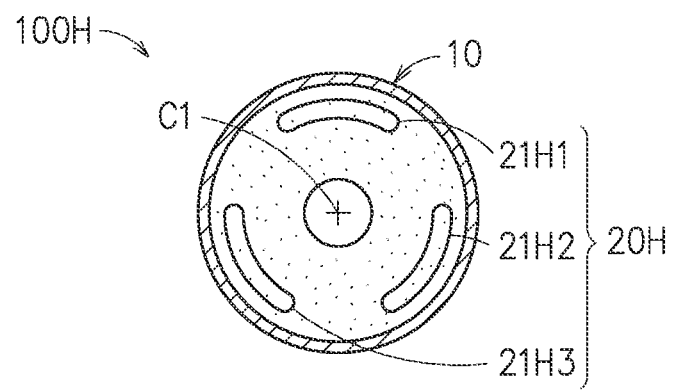
FIG. 8B is a schematic cross-sectional view of another exemplary example of this disclosure that three arc-shape coil sets are evenly arranged; around the first axis.

Referring now to the embodiment shown in FIG. 8B, the neuromodulation probe 100H includes a body 10 and a coil set 20H consisted of three coils 21H1, 21H2, 21H3 evenly and symmetrically arranged to surround the first axis C1 of the body 10. Each of these three coils 21H1, 21H2, 21H3 has an arc-shaped cross section. That is, the conductive wire for forming each of the three coils 21H1, 21H2, 21H3 is no longer to be wound about the second axis C2, but to be wound to form a coil extending along the second axis C2 and having an arc-shape cross section centered at the second axis C2.

From the embodiment of FIG. 8B, it is explained that the cross section available for the coil of the neuromodulation probe according to this disclosure can be a regular or irregular shape, not limited to any specific shape in the radial cross section. In FIG. 8B, the arc-shape coils 21H1, 21H2, 21H3 can also be applied to any embodiment from FIG. 1 to FIG. 8A.

To summarize the embodiments from FIG. 1 to FIG. 8B, it is understood that the arrangement of the coil set, the coil and the associated cross section can be versatile but simply characterized in having the second axis of the coil parallel (or even collinear) to the first axis thereof. On the other hand, the intensity, frequency and flow direction of the electric current, the wire diameter, winding number and pitch diameter of the coil, and the length and diameter of the body are not specifically limited, but determined per practical requirements for reaching necessary stimulation intensity.

The body in any of the aforesaid embodiments is shown to be a lengthy circular tube. However, the body of this disclosure can also be designed in other shapes, such as a regular or irregular geometric arc shape. In addition, the coils in the same body can be independently controlled to provide versatile energy output patterns.

It is proved that, when the extension direction of the coil (i.e., the current direction) is roughly perpendicular to the nerve fiber, the nerve fiber would not be affected to induce obvious variation in action potential. On the other hand, if the extension direction of the coil (i.e., the current direction) is roughly parallel to the nerve fiber, then the nerve fiber would be easily affected to vary the action potential so as further to induce neural stimulation response. Thus, by applying the neuromodulation probe having the lengthy tube-shaped body in accordance with this disclosure to human body such as the brain, if the neuromodulation probe is positioned to a side of the nerve fiber, then, after the coils of the neuromodulation probe are energized, the nerve fibers extending perpendicular to the electric current would not be affected to change the corresponding action potentials. Thereupon, possible side effects such as muscle stiffness caused by stimulating the nerve fiber can be reduced. However, for the nerve fiber to be stimulated or tested, the parallel arrangement between the current direction and the target nerve fiber can make easy to achieve expected response from the electrical stimulation.

Similarly, to the bodies with irregular shape such as a stick pad, by applying the neuromodulation probe of this disclosure to the nerve fiber according to its extending direction, then the electrical stimulation can be easily performed upon the target nerve fiber. In addition, according to different practical situations, the coils to provide different extension directions would allow the neuromodulation probe of this disclosure to perform directional testing upon an area having various extending directions of the local nerve fibers.

By having the embodiment of FIG. 4 as an example, the design of the coil can follow the equation (1):

$$B = \mu \times I \times n$$

in which B: magnetic field (Tm), μ: magnetic permeability ($4 \times 10^{-7}$ for example), I: electric current (A), and n: winding number of the coil.

If the distance D is set to be greater than or equal to 1 mm, the height h of each of the coils 21C1, 21C2, 21C3 is 1.5 mm, the electric current I is 40 mA, and the specification of each of the coils 21C1, 21C2, 21C3 is an US AWG40 enameled wire, then the winding number n of the coil is 16.

By having the embodiment of FIG. 4A as an example, given that d: center distance between the two coils 21C2, 21C3, r: radius of the coil 21C2, and R: radius of the body 10. The equation (2) is as follows:

$$\frac{d}{2 \times \sqrt{3}} \times 2 = R - r$$

If d/2=3r, R=1.3 mm, and r=0.29 mm, then the field potential would be 33.3 mv/mm.

If d/2=4r, R=1.3 mm, and r=0.23 mm, then the field potential would be 10 mv/mm.

Figure 9A:
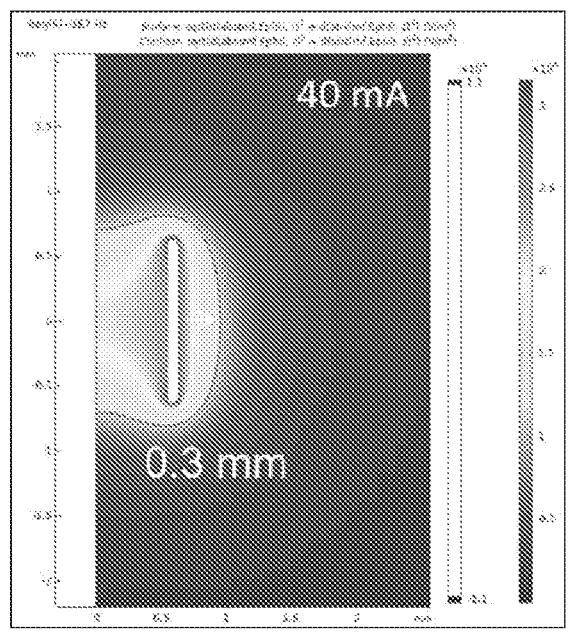
FIG. 9A and FIG. 9B demonstrate schematically ranges of effect by controlling frequencies of the electric current in accordance with this disclosure.
Figure 9B:
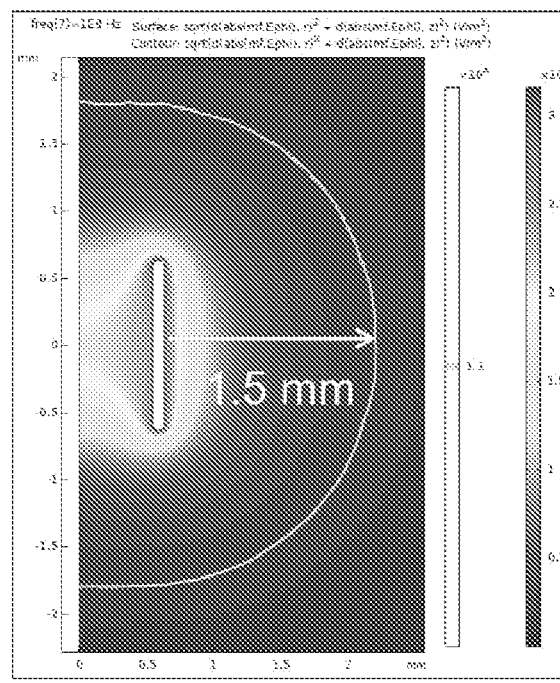

According to the aforesaid two equations (1), (2), it can be understood that thus disclosure can evaluate the specifications of the coils and the body to design the necessary electric current, and different electric currents would lead to different stimulation ranges. As shown in FIG. 9A, if the frequency of the electric current is 10 MHz, the range of effect of the magnetic field would be about 0.3 mm. On the other hand, as shown in FIG. 9B, if the frequency of the electric current is about 100 MHz, then the corresponding range of effect of the magnetic field would be about 1.5 mm.

Refer now to FIG. 3, FIG. 3A, and FIG. 10A through FIG. 10D. By having the embodiment of FIG. 3 and FIG. 3A as an embodiment, given that the wire for forming the coil 21B1 or 21B2 has a diameter of 0.36 mm, the internal coil 21B1 has a pitch diameter D1 of 6 mm, the external coil 21B2 has a pitch diameter D2 of 13 mm, and the winding numbers of the coils 21B1, 21B2 are both 16, then different arrangements for directions and voltages of the corresponding electric currents flowing in the coils 21B1, 21B2 would generate four results illustrated in FIG. 10A through FIG. 10D.

Figure 10A:
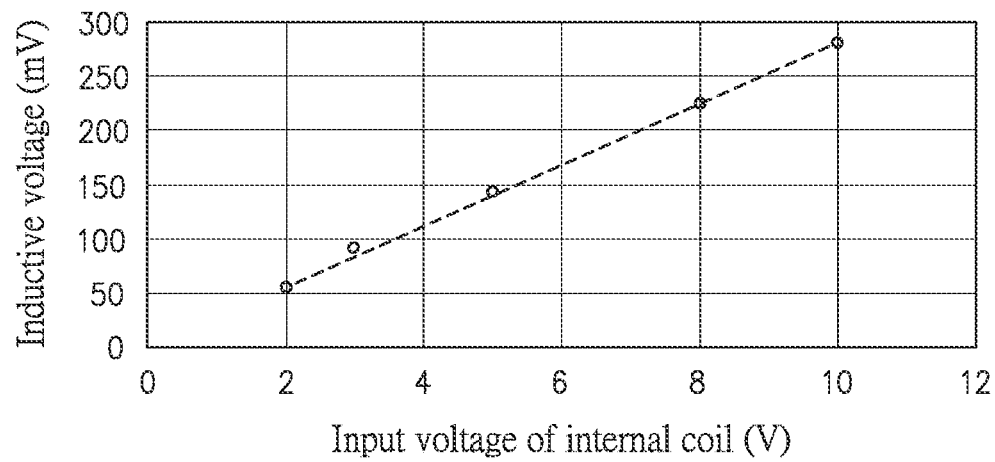
FIG. 10A to FIG. 10D demonstrate schematically relationships between the inductive voltages and the input voltages by modulating the dual coil set of FIG. 3.

In FIG. 10A, the electric currents of the two coils 21B1, 21B2 have the same flow direction, the voltage of the internal coil 21B1 is modulated, and the voltage of the external coil 21B2 is fixed.

Figure 10B:
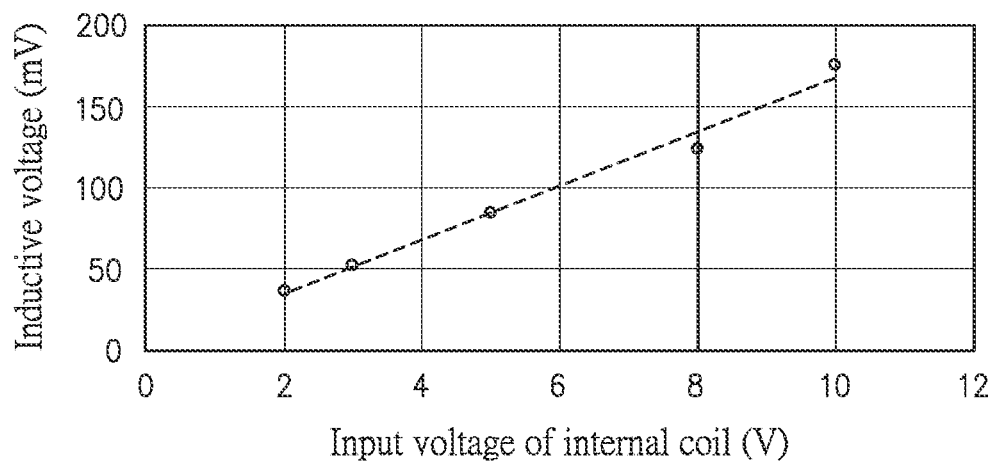

FIG. 10B, the electric currents of the two coils 21B1, 21B2 have reverse flow directions, the voltage of the internal coil 21B1 is modulated, and the voltage of the external coil 21B2 is fixed.

Figure 10C:
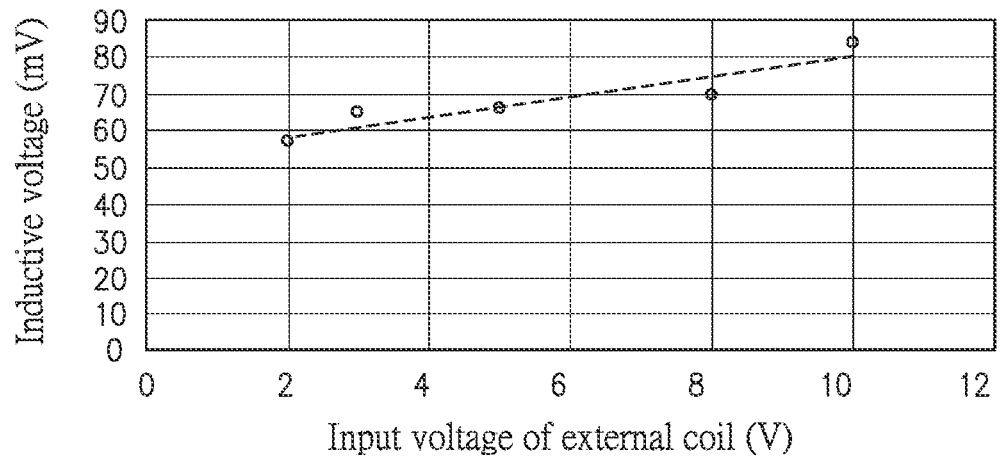

FIG. 10C, the electric currents of the two coils 21B1, 21B2 have the same flow direction, the voltage of the internal coil 21B1 is fixed, and the voltage of the external coil 21B2 is modulated.

Figure 10D:
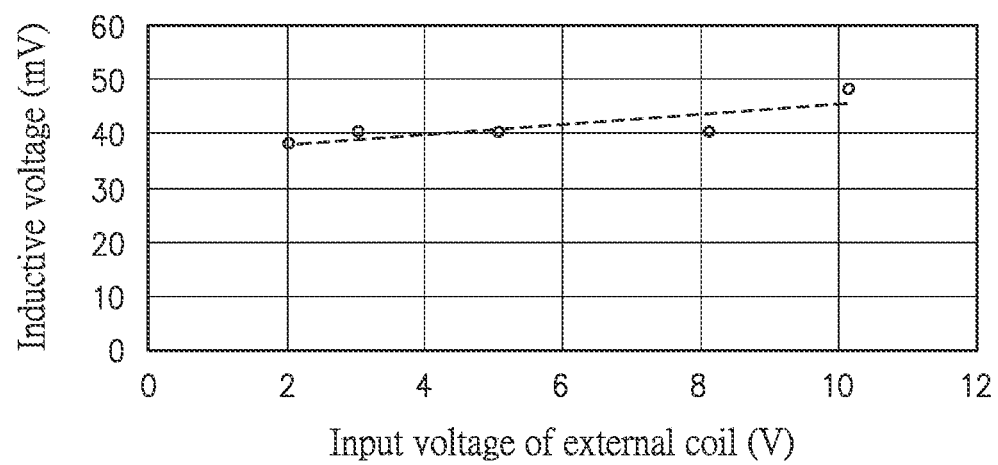

FIG. 10D, the electric currents of the two coils 21B1, 21B2 have reverse flow directions, the voltage of the internal coil 21B1 is fixed, and the voltage of the external coil 21B2 is modulated.

FIG. 10A to FIG. 10D show four different relationships, from which the independent controllability of the coils of the embodiment shown in FIG. 3 and FIG. 3A in voltage, current direction and magnetic-field intensity can be demonstrated. In one exemplary, only one of the coils 21B1, 21B2 is energized via the electric current, and another thereof can be electrically charged though induction of the electric current.

In summary, the neuromodulation probe provided by this disclosure utilizes the coil-type electrodes to flow the electric current for generating the magnetic field, such that the nerve fiber extending in the specific cross-sectional direction can be polarized to produce the action potential. The coil flowing the electric current is perpendicular to the extending direction of the nerve fiber to be stimulated, so that the selectivity in the direction of electrical stimulation can be obtained. Thereupon, influence upon the nerve fibers adjacent to the nerve fiber to be stimulated would be substantially decreased, and thus the associated side effects from the electrical stimulation can be effectively reduced.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A neuromodulation probe, comprising:
a body, having a first axis and a length along the first axis; and
a plurality of coil sets disposed coaxially and separately along the first axis, wherein a distance to separate adjacent two of the plurality of coil sets is greater than or equal to zero, wherein each coil set includes at least one coil, the at least one coil being formed by winding spirally a conductive wire plural times about a second axis inside the body, the second axis being parallel to the first axis, wherein the at least one coil has two opposite wire ends for providing an electric current to flow in or out of the at least one coil wherein the at least one coil is coated with an insulation layer or a polymer layer.

2. The neuromodulation probe of claim 1, wherein each of the plurality of coil sets has a coil disposing coaxially and orderly to each other.

3. The neuromodulation probe of claim 1, wherein each of the plurality of coil sets has a plurality of coils, and the plurality of coils are sleeved to each other by centering at the first axis.

4. The neuromodulation probe of claim 1, wherein each of the plurality of coil sets has a plurality of coils, and the plurality of coils are radially separated but surround commonly the first axis of the body.

5. The neuromodulation probe of claim 1, wherein the plurality of coils have the same or different flow directions, intensities and frequencies of electric currents.

6. The neuromodulation probe of claim 1, wherein the at least one coil and the body are arranged in a coaxial setting manner.

7. Neuromodulation probe of claim 1, wherein the coil has an arc-shape cross section.

8. The neuromodulation probe of claim 1, wherein the at least one coil set is fixed inside the body by a fixing glue.

9. The neuromodulation probe of claim 1, wherein the body is furnished thereinside with an internal lengthy space extending along the first axis for providing a channel to contain a coolant inside the body.

10. The neuromodulation probe of claim 1, further including at least one sub coil set, wherein the at least one sub coil set includes at least one sub coil formed by winding another conductive wire plural times about a third axis inside the body, the third axis is perpendicular to the first axis, the at least one sub coil has two opposite wire ends for providing an electric current to flow in and out of the at least one sub coil, and the at least one sub coil set and the at least one coil set are arranged in an interleaved setting manner.

11. The neuromodulation probe of claim 10, wherein the at least one coil and the at least one sub coil have the same or different flow directions, intensities and frequencies of electric currents.

* * * * *